United States Patent [19]

Kusaba et al.

[11] Patent Number: 4,841,088
[45] Date of Patent: Jun. 20, 1989

[54] IODOPROPARGYL CARBAMATE DERIVATIVE, A METHOD FOR ITS PRODUCTION AND FUNGICIDAL COMPOSITIONS CONTAINING IT AS AN ACTIVE INGREDIENT

[75] Inventors: Tomoyuki Kusaba, Toyonaka; Junya Takahashi, Hyogo; Masayo Sugano, Osaka; Tamon Uematsu, Kobe; Yukio Oguri, Toyonaka; Tomohiro Teramae, Takarazuka, all of Japan

[73] Assignee: Sumitomo Chemical Company, Limited, Osaka, Japan

[21] Appl. No.: 84,885

[22] Filed: Aug. 13, 1987

[30] Foreign Application Priority Data

Aug. 26, 1986 [JP] Japan .................. 61-200274
Aug. 26, 1986 [JP] Japan .................. 61-200276
Dec. 22, 1986 [JP] Japan .................. 61-307390
Dec. 23, 1986 [JP] Japan .................. 61-315812

[51] Int. Cl.$^4$ ................................ C07C 121/52
[52] U.S. Cl. ......................... 558/417; 560/18; 560/22; 560/29; 560/30; 560/33; 560/17; 514/535; 558/416;
[58] Field of Search ............. 558/417; 560/33; 514/478, 524, 535

[56] References Cited

U.S. PATENT DOCUMENTS

| | | | |
|---|---|---|---|
| 3,515,744 | 6/1970 | Steinbrunn | 558/417 |
| 3,923,870 | 12/1975 | Singer | 106/18.2 |
| 4,259,350 | 3/1981 | Morisawa et al. | 514/535 |
| 4,474,807 | 10/1984 | Gerhardt et al. | 514/478 |
| 4,752,615 | 6/1988 | Takahashi et al. | 514/535 |

FOREIGN PATENT DOCUMENTS

| | | |
|---|---|---|
| 0014032 | 8/1980 | European Pat. Off. ........ 560/33 |
| 0015044 | 9/1980 | European Pat. Off. ........ 560/33 |
| 0093620 | 11/1983 | European Pat. Off. ........ 558/417 |
| 1400995 | 7/1964 | France ........ 560/33 |
| 40-3903 | 3/1965 | Japan . |
| 230119 | 3/1969 | U.S.S.R. . |
| 2138292 | 10/1984 | United Kingdom . |
| 2140299 | 11/1984 | United Kingdom . |

OTHER PUBLICATIONS

Khim. Farm. Zh., 19, No. 12, 1445-1456 (1985) w/Abstract (PESTDOC, 86-84488).
Chem. Abstracts, 96, 173935u (1982).

*Primary Examiner*—William R. Dixon, Jr.
*Assistant Examiner*—Jerry D. Johnson
*Attorney, Agent, or Firm*—Stevens, Davis, Miller & Mosher

[57] ABSTRACT

A compound having a fungicidal activity represented by the general formula,

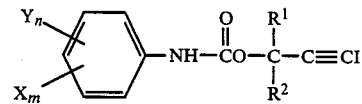

wherein X, which may be the same or different, represents a cyano, nitro, halogenated lower alkyl, $C_1$-$C_{12}$ alkoxy, lower alkoxy-substituted lower alkyl, lower alkenyloxy, lower alkynyloxy, halogenated lower alkoxy, lower alkoxycarbonyl or lower alkylthio group, $R^1$ and $R^2$, which may be the same or different, represent a hydrogen atom or a methyl group, Y represents a hydrogen or chlorine atom, m represents an integer of from 1 to 5, and n represents an integer of from 0 to 4, the sum of m and n being less than 6.

6 Claims, No Drawings

IODOPROPARGYL CARBAMATE DERIVATIVE, A METHOD FOR ITS PRODUCTION AND FUNGICIDAL COMPOSITIONS CONTAINING IT AS AN ACTIVE INGREDIENT

The present invention relates to an iodopropargyl carbamate derivative, its production and agricultural and horticultural fungicides containing it as an active ingredient.

Hitherto, dithiocarbamate compounds such as Maneb, Mancozeb, etc. and phthalimide compounds such as Captan, Difolatan, etc. are on the market as an agricultural and horticultural fungicide having a wide antimicrobial activity and finding wide applications.

However, the foregoing agricultural and horticultural fungicides such as Maneb, Mancozeb, Captan, Difolatan, etc., in spite of their wide antimicrobial activity, may not always be said to have a practical controlling effect against all diseases, and besides the fact is that they should be applied in a very high concentration of 1-2 kg/ha as expressed by the amount of active ingredient. Said fungicides, therefore, may not always be said to be satisfactory as an agricultural and horticultural fungicide.

In view of the situation like this, the present inventors extensively studied to develop excellent agricultural and horticultural fungicides, and as a result, found that the carbamate derivative having an iodopropargyl group of the present invention is a compound having few problems described above and excellent fungicidal activity. The present inventors thus attained to the present invention.

The present invention provides a carbamate derivative represented by the general formula (I) (hereinafter referred to as present compound),

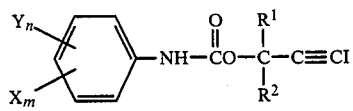

wherein X, which may be the same or different, represents a cyano, nitro, halogenated lower alkyl, $C_1$-$C_{12}$ alkoxy, lower alkoxy-substituted lower alkyl, lower alkenyloxy, lower alkynyloxy, halogenated lower alkoxy, lower alkoxycarbonyl or lower alkylthio group, $R^1$ and $R^2$, which may be the same or different, represent a hydrogen atom or a methyl group, Y represents a hydrogen or chlorine atom, m represents an integer of from 1 to 5, and n represents an integer of from 0 to 4, the sum of m and n being less than 6, its production and agricultural and horticultural fungicides containing it as an active ingredient.

For plant diseases which can be controlled with the present compounds, there are given downy mildew of vegetables and Japanese radish (*Peronospora brassicae*), downy mildew of spinach (*Peronospora spinaciae*), downy mildew of tobacco (*Peronospora tabacina*), downy mildew of cucumber (*Pseudoperonospora cubensis*), downy mildew of grape (*Plasmopara viticola*), downy mildew of dropwort (*Plasmopara nivea*), late blight of apple, strawberry and ginseng (*Phytophthora cactorum*), phytophthora rot of tomato and cucumber (*Phytophthora capsici*), late blight of pineapple (*Phytophthora cinnamomi*), late blight of potato, tomato and eggplant (*Phytophthora infestans*), late blight of tobacco, broad bean and Welsh onion (*Phytophthora nicotianae* var. *nicotianae*), damping-off of spinach (Pythium sp.), damping-off of cucumber (*Pythium aphanidermatum*), browning root rot of wheat (Pythium sp.), damping-off of tobacco (*Pythium debaryanum*), pythium rot of soybean (*Pythium aphanidermatum, P. debaryanum, P. irregulare, P. myriotylum, P. ultimam*), blast of rice (*Pyricularia oryzae*), brown spot of rice (*Cochliobolus miyabeanus*), scab of apple (*Venturia inaequalis*), canker of apple (*Valsa mali*), alternaria leaf spot of apple (*Alternaria mali*), black spot of pear (*Alternaria kikuchiana*), scab of pear (*Venturia nashicola*), melanose of citrus (*Diaporthe citri*), common green mold of citrus (*Penicillium digitatum*), blue mold of citrus (*Penicillium italicum*), phomopsis rot of peach (Phomopsis sp.), anthracnose of Japanese persimmon (*Gloeosporium kaki*), leaf spot of Japanese persimmon (*Cercospora kaki, Mycosphaerella nawae*), ripe rot of grape (*Glomerella cingulata*), gray mold of grape (*Botrytis cinerea*), stripe of barley (*Helminthosporium gramineum*), loose smut of barley (*Ustilago nuda*), speckled leaf blotch of wheat (*Septoria tritici*), glume blotch of wheat (*Leptosphaeria nodorum*), eye spot of wheat (*Pseudocercosporella herpotrichoides*), powdery mildew of wheat and barley (*Erysiphe graminis*), rust of wheat and barley (*Puccinia graminis, P. striiformis, P. recondita*), anthracnose of melons (*Colletotrichum lagenarium*), gummy stem blight of melons (*Mycosphaerella melonis*), powdery mildew of melons (*Sphaerotheca fuliginea*), early blight of tomato (*Alternaria solani*), brown spot of tobacco (*Alternaria longipes*), anthracnose of tobacco (*Colletotrichum tabacum*), cercospora leaf spot of beet (*Cercospora beticola*), early blight of potato (*Alternaria solani*), brown leaf spot of peanut (*Cercospora arachidicola*), septoria brown spot of soybean (*Septoria glycines*), melanose of soybean (*Diaporthe phaseololum*), anthracnose of soybean (*Colletotrichum sp.*), purple stain of soybean (*Cercospora kikuchii*), etc.

From the standpoint of fungicidal activity, the present compounds are more preferably a compound represented by the general formula,

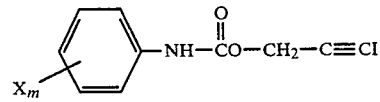

wherein X, which may be the same or different, represents a cyano, nitro, halogenated $C_1$-$C_3$ alkyl, $C_1$-$C_{12}$ alkoxy, $C_1$-$C_4$ alkoxy-substituted $C_1$-$C_3$ alkyl, $C_2$-$C_4$ alkenyloxy, $C_3$-$C_5$ alkynyloxy, halogenated $C_1$-$C_4$ alkoxy, $C_1$-$C_3$ alkoxycarbonyl or $C_1$-$C_4$ alkylthio group, and m represents an integer of from 1 to 5, and particularly preferably a compound represented by the general formula,

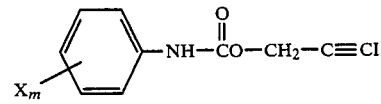

wherein X, which may be the same or different, represents a cyano, nitro, halogenated $C_1$-$C_2$ alkyl or $C_1$-$C_5$ alkoxy group, and m represents an integer of from 1 to 3.

A method for producing the present compounds will be explained in detail. The present compounds are produced through the following representative synthetic routes.

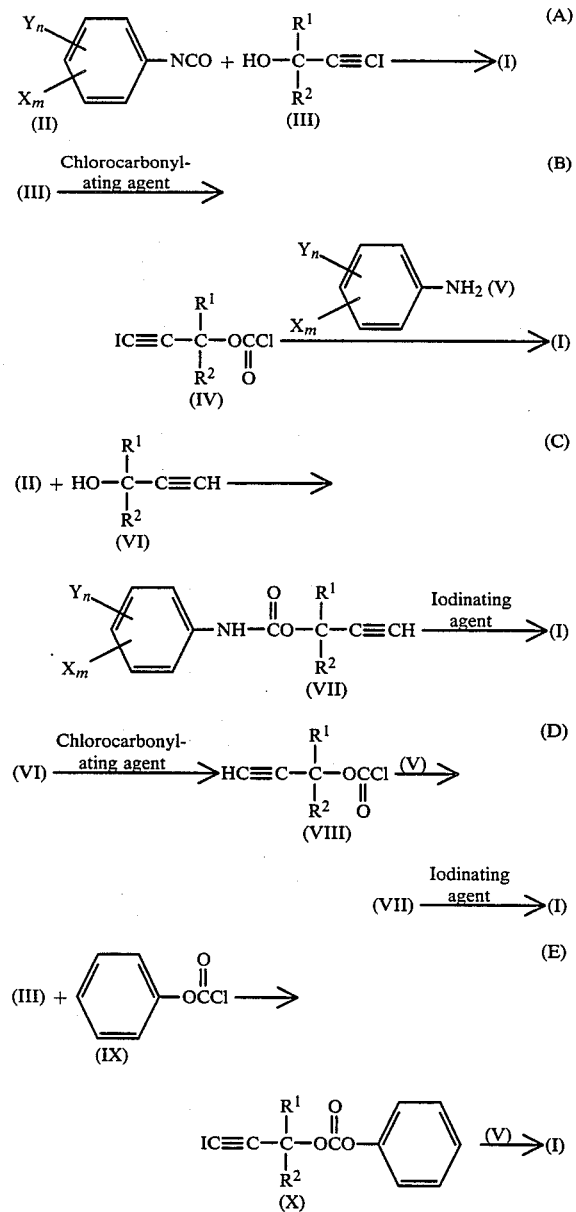

In the above formulae, X, Y, $R^1$, $R^2$, m and n represent the same meaning as described above.

METHOD A

This is a method of reacting a phenyl isocyanate derivative represented by the general formula (II) with an iodopropargyl alcohol derivative represented by the general formula (III).

In the above reaction, the reaction temperature is normally from −10° to 100° C., and the reaction time is normally from a moment to 12 hours. As to the amounts of the reagents used in this reaction, the amount of the iodopropargyl alcohol derivative represented by the general formula (III) is from 0.9 to 2 equivalents based on 1 equivalent of the phenyl isocyanate derivative represented by the general formula (II).

In the above reaction, a reaction solvent is not always necessary, but generally the reaction is carried out in the presence of a solvent. The solvent usable includes for example aromatic hydrocarbons (e.g. benzene, toluene), ethers (e.g. diethyl ether, tetrahydrofuran), halogenated hydrocarbons (e.g. dichloromethane, chloroform), and mixtures thereof.

In the above reaction, a catalyst is not always necessary, but the reaction can be promoted by adding the catalyst. The catalyst usable includes tertiary amines (e.g. pyridine, triethylamine, diethylaniline), tin compounds (e.g. tetra-n-butyltin, di-n-butyltin chloride), Lewis acids (e.g. boron trifluoride, aluminum chloride), etc.

METHOD B

This is a method of reacting an iodopropargyl alcohol derivative represented by the general formula (III) with a chlorocarbonylating agent to obtain a chlorocarbonate derivative represented by the general formula (IV) and then reacting the resulting chlorocarbonate derivative with an aniline derivative represented by the general formula (V).

Firstly, in the reaction of the iodopropargyl alcohol derivative represented by the general formula (III) with the chlorocarbonylating agent, phosgene, etc. are used as said agent.

In the above reaction, the reaction temperature is normally from −10° C. to room temperature, and the reaction time is normally from a moment to 12 hours. This reaction is carried out in the presence of an acid-binding agent, and this agent includes for example tertiary amines such as pyridine, triethylamine, N,N-diethylaniline, quinoline, etc.

As to the amounts of the reagents used in this reaction, the amount of the chlorocarbonylating agent is from 0.9 to 2 equivalents based on 1 equivalent of the iodopropargyl alcohol derivative represented by the general formula (III), and that of the acid-binding agent is from 0.9 to 2 equivalents based on 1 equivalent of the same.

Normally, the above reaction is carried out in the presence of a solvent, and the solvent usable includes for example aromatic hydrocarbons (e.g. benzene, toluene), halogenated hydrocarbons (e.g. dichloromethane, chloroform), etc.

Secondly, in the reaction of said chlorocarbonate derivative represented by the general formula (IV) with the aniline derivative represented by the general formula (V), the reaction temperature is normally from −10° to 100° C., and the reaction time is normally from a moment to 12 hours.

This reaction is carried out in the presence or absence of an acid-binding agent, but generally, it is carried out in the presence of an acid-binding agent. The agent usable includes for example tertiary amines (e.g. pyridine, triethylamine, N,N-diethylaniline), alkali metal hydroxides (e.g. sodium hydroxide, potassium hydroxide), etc.

As to the amounts of the reagents used in this reaction, the amount of the aniline derivative represented by the general formula (V) is from 0.9 to 2.0 equivalents based on 1 equivalent of the chlorocarbonate derivative represented by the general formula (IV), and that of the acid-binding agent is from 0.9 to 2.0 equivalents based on 1 equivalent of the same.

Normally, the above reaction is carried out in the presence of a solvent, and the solvent usable includes for example aromatic hydrocarbons (e.g. benzene, toluene), halogenated hydrocarbons (e.g. dichloromethane, chloroform), etc.

METHOD C

This is a method of reacting a phenyl isocyanate derivative represented by the general formula (II) with a propargyl alcohol derivative represented by the general formula (VI) to obtain a carbamate derivative represented by the general formula (VII) and then reacting the resulting carbamate derivative with an iodinating agent, preferably, in the presence of an alkali.

The reaction of the phenyl isocyanate derivative represented by the general formula (II) with the propargyl alcohol derivative represented by the general formula (VI) can be carried out according to Method A.

In the reaction of the carbamate derivative represented by the general formula (VII) with the iodinating agent, the alkali usable includes for example alkali metal hydroxides (e.g. sodium hydroxide, potassium hydroxide), and the iodinating agent includes for example iodine.

In the above reaction, the reaction temperature is normally from $-10°$ C. to room temperature, and the reaction time is normally from 1 to 12 hours. As to the amounts of the reagents used in this reaction, any of the amounts of the iodinating agent and alkali is from 1 to 1.5 equivalents based on 1 equivalent of the carbamate derivative represented by the general formula (VII).

METHOD D

This is a method of reacting a propargyl alcohol derivative represented by the general formula (VI) with a chlorocarbonylating agent to obtain a chlorocarbonate represented by the general formula (VIII), reacting the resulting chlorocarbonate with an aniline derivative represented by the general formula (V) to obtain a carbamate derivative represented by the general formula (VII), and then reacting the resulting carbamate derivative with an iodinating agent, preferably in the presence of an alkali.

The reaction of the propargyl alcohol derivative represented by the general formula (VI) with the chlorocarbonylating agent, and that of the chlorocarbonate derivative represented by the general formula (VIII) with the aniline derivative represented by the general formula (V) can be carried out according to Method B. The reaction of the carbamate derivative represented by the general formula (VII) with the iodinating agent is carried out in the similar manner to the iodination in Method C.

METHOD E

This is a method of reacting an iodopropargyl alcohol derivative represented by the general formula (III) with phenyl chloroformate represented by the formula (IX) to obtain a carbonate derivative represented by the general formula (X), and then reacting the resulting carbonate derivative with an aniline derivative represented by the general formula (V).

Firstly, in the reaction of the iodopropargyl alcohol derivative represented by the general formula (III) with phenyl chloroformate represented by the formula (IX), the reaction temperature is normally from $-10°$ C. to room temperature, and the reaction time is normally from a moment to 12 hours. This reaction is carried out in the presence of an acid-binding agent, and the agent usable includes for example tertiary amines such as pyridine, triethylamine, N,N-diethylaniline, quinoline, etc. As to the amounts of the reagents used in this reaction, the amount of phenyl chloroformate represented by the formula (IX) is from 0.9 to 2 equivalents based on 1 equivalent of the iodopropargyl alcohol derivative represented by the general formula (III), and that of the acid-binding agent is from 0.9 to 2 equivalents based on 1 equivalent of the same.

Normally, the above reaction is carried out in the presence of a solvent, and the solvent usable includes for example aromatic hydrocarbons (e.g. benzene, toluene), halogenated hydrocarbons (e.g. dichloromethane, chloroform), etc.

Secondly, in the reaction of the carbonate derivative represented by the general formula (X) with the aniline derivative represented by the general formula (V), the reaction temperature is normally from $-10°$ to $100°$ C., and the reaction time is normally from a moment to 12 hours. This reaction is carried out in the presence or absence of an acid-binding agent, and generally, it is carried out in the presence of an acid-binding agent. The agent usable includes for example tertiary amines such as pyridine, triethylamine, N,N-diethylaniline, etc., alkaline metal hydride such as sodium hydride, etc.

As to the amounts of the reagents used in this reaction, the amount of the aniline derivative represented by the general formula (V) is from 0.9 to 2.0 equivalents based on 1 equivalent of the carbonate derivative represented by the general formula (X), and that of the acid-binding agent is from 0.9 to 1.5 equivalents based on 1 equivalent of the same.

Normally, the above reaction is carried out in the presence of a solvent, and the solvent usable includes for example aromatic hydrocarbons (e.g. benzene, toluene), halogenated hydrocarbons (e.g. dichloromethane, chloroform), etc.

Hereupon, the iodopropargyl alcohol derivative represented by the general formula (III) can be obtained by iodinating commercially available propargyl alcohol according to the method described in J. Am. Chem. Soc., 102, 4193–4198 (1980).

When the present compounds are used as an active ingredient for fungicides, they may be used as they are without adding any other ingredients. Generally, however, they are formulated before use into emulsifiable concentrates, wettable powders, suspension formulations, dusts, liquid formulations, etc. by mixing with solid carriers, liquid carriers, surface active agents and other auxiliaries for formulation. In this case, the content of the present compounds, which are active ingredients, in these preparations is from 0.1 to 99.9%, preferably from 1 to 90%.

The solid carriers include fine powders or granules of kaolin clay, attapulgite clay, bentonite, terra abla, pyrophyllite, talc, diatomaceous earth, calcite, corn stalk powder, walnut shell powder, urea, ammonium sulfate, synthetic hydrated silicon dioxide, etc. The liquid carriers include aromatic hydrocarbons (e.g. xylene, methylnaphthalene), alcohols (e.g. isopropanol, ethylene glycol, cellosolve), ketones (e.g. acetone, cyclohexane, isophorone), vegetable oils (e.g. soybean oil, cotton seed oil), dimethyl sulfoxide, acetonitrile, water, etc. The surface active agents used for emulsification, dispersion, wetting, etc. include anionic surface active agents such as the salt of alkyl sulfates, alkyl(aryl)sulfonates, dialkyl sulfosuccinates, the salt of polyoxyethylene alkylaryl ether phosphoric acid esters, naphthalene-sulfonic acid/formalin condensates, etc. and nonionic surface active agents such as polyoxyethylene alkyl ether, polyoxyethylene polyoxypropylene block copolymers, sorbitan fatty acid esters, polyoxyethylene sorbitan fatty acid esters, etc. The auxiliaries for formulation include lignosulfonates, alginates, polyvinyl alcohol, gum arabic, CMC (carboxymethyl cellulose), PAP (isopropyl acid phosphate), etc.

A method for applying the present compounds as agricultural and horticultural fungicides includes for example foliar application, solid treatment, seed disinfection, etc., but any of the methods generally used by those skilled in the art exhibits a sufficient effect.

When the present compounds are used as an active ingredient for agricultural and horticultural fungicides, their dosage rate varies with crops and diseases aimed at, degree of outbreak of diseases, preparation forms, application methods, application time, weather conditions, etc., but it is generally from 0.5 to 200 g/are. When the emulsifiable concentrates, wettable powders, suspension formulations, liquid formulations, etc. are applied in dilution with water, the application concentration of the present compounds is from 0.005 to 0.5%, preferably from 0.01 to 0.2%. The dusts, granules, etc. are applied as they are without dilution.

Further, the present compounds can be used as agricultural and horticultural fungicides for plow fields, paddy fields, orchards, tea gardens, pastures, turfs, etc., and also an increase in the fungicidal activity can be expected by using them in mixture with other agricultural and horticultural fungicides. In addition, they can be used in mixture with insecticides, acaricides, nematocides, herbicides, plant growth regulators, fertilizers, etc.

The present invention will be illustrated in more detail with reference to the following production examples, formulation exaples and test examples, but the present invention is not limited to these examples.

PRODUCTION EXAMPLE 1

To 30 ml of a dry tetrahydrofuran solution containing 1.1 g (5 mmoles) of 1,1-dimethyl-3-iodopropargyl alcohol and one drop of triethylamine was added at a time 0.7 g (5 mmoles) of 4-ethoxyphenyl isocyanate at room temperature. After stirring for 10 hours, the solvent was removed by vaporization under reduced pressure. The residue was recrystallized from chloroform to obtain 0.4 g of 1,1-dimethyl-3-iodopropargyl N-(4-ethoxyphenyl)carbamate.

m.p., 134°–135° C.

$^1$H-NMR (CDCl$_3$):δ(ppm) 1.39 (3H, t, J=7Hz), 1.70 (6H, s), 3.96 (2H, q, J=7Hz), 6.42 (1H, brs) 6.76 (2H, d, J=9Hz), 7.23 (2H, d, J=9Hz)

PRODUCTION EXAMPLE 2

To 30 ml of a dry tetrahydrofuran solution containing 0.9 g (5 mmoles) of 3-iodopropargyl alcohol and one drop of triethylamine was added at a time 0.8 g (5 mmoles) of 4-nitrophenyl isocyanate at room temperature. After stirring for 10 hours, the solvent was removed by vaporization under reduced pressure. The residue was recrystallized from chloroform to obtain 0.38 g of 3-iodopropargyl N-(4-nitrophenyl)carbamate.

m.p., 150°–151° C.

$^1$H-NMR (DMSO-d$_6$):δ(ppm) 4.91 (2H, s), 7.65 (2H, d, J=11Hz), 8.19 (2H, d, J=11Hz)

PRODUCTION EXAMPLE 3

To 10 ml of a dry ether solution containing 3 g (30 mmoles) of phosgene was gradually added dropwise 10 ml of a dry ether solution containing 0.84 g (15 mmoles) of propargyl alcohol and 1.94 g (15 mmoles) of quinoline at 0° C. with stirring. After addition, the reaction mixture was stirred at room temperature for 2 hours, washed with dilute hydrochloric acid and dried over anhydrous sodium sulfate, and the solvent was removed by vaporization at atmospheric pressure.

The residue was dissolved in 10 ml of dry ether, and to the resulting solution was added dropwise 3.6 g (30 mmoles) of 3-methoxyaniline with ice-cooling. Thereafter, stirring was continued for 5 hours at room temperature. The reaction mixture was washed with dilute hydrochloric acid and dried over sodium sulfate, and ether was removed by vaporization under reduced pressure. The residue was dissolved in 25 ml of a methanol solution containing 0.6 g (15 mmoles) of sodium hydroxide, and to the resulting solution was added 3.8 g (15 mmoles) of iodine with ice-cooling, followed by stirring at room temperature for 2 hours. The reaction solution was poured into 100 ml of ice water and extracted with ethyl acetate, and after liquid-liquid separation, the organic layer was washed with an aqueous sodium hydrogensulfite solution and then with water. After drying over anhydrous sodium sulfate, the solvent was removed by vaporization under reduced pressure. The residue was collected and treated by thin layer chromatography (thickness, 2 mm; n-hexane: ethyl acetate=4:1) to obtain 0.5 g of 3-iodopropargyl N-(3-methoxyphenyl)carbamate.

m.p., 106.5°–107.0° C.

$^1$H-NMR (CDCl$_3$):δ (ppm) 3.75 (3H, s), 4.89 (2H, s), 6.4–7.4 (4H, m)

PRODUCTION EXAMPLE 4

To 10 ml of a chloroform solution containing 0.91 g (5 mmoles) of 3-iodopropargyl alcohol and a few drops of triethylamine was added at a time 0.75 g (5 mmoles) of 4-methoxyphenyl isocyanate at room temperature. After stirring at the same temperature for 3 hours, the formed solid was collected by filtration and washed with a small amount of chloroform. The solid obtained was recrystallized from ethyl acetate to obtain 0.5 g of 3-iodopropargyl N-(4-methoxyphenyl)carbamate.

m.p., 135°–136° C.

$^1$H-NMR (CDCl$_3$+DMSO-d$_6$):δ(ppm) 3.75 (3H, s), 4.88 (3H, s), 6.80 (2H, d, J=11Hz), 7.24 (2H, d, J=11Hz), 8.20 (1H, brs)

PRODUCTION EXAMPLE 5

To 10 ml of chloroform solution containing 1.00 g (5.5 mmoles) of 3-iodopropargyl alcohol and a few drops of triethylamine was added at a time 1 g (5.2 mmoles) of 4-isobutoxyphenyl isocyanate at room temperature. After stirring overnight at the same temperature, the formed solid was collected by filtration and washed with a small amount of chloroform. The solid obtained was recrystallized from ethyl acetate/n-hexane to obtain 0.3 g of 3-iodopropargyl N-(4-isobutoxyphenyl)carbamate.

m.p., 102°–103° C.

$^1$H-NMR (CDCl$_3$):δ(ppm) 1.01 (6H, d, J=6Hz), 2.09 (1H, m), 3.70 (2H, d, J=6Hz), 6.69 (1H, brs), 6.84 (2H, d, J=8Hz), 7.25 (2H, d, J=8Hz)

PRODUCTION EXAMPLE 6

To 45 ml of a dichloromethane solution containing 5.80 g (32 mmoles) of 3-iodopropargyl alcohol and 4.85 g (48 mmoles) of triethylamine was added dropwise 5 g (32 mmoles) of phenyl chloroformate with ice-cooling. After completion of the addition, stirring was contained at room temperature for 1 hour. The reaction solution was washed with 1N aqueous hydrochloric acid and dried over anhydrous magnesium sulfate, and the solvent was removed by vaporization under reduced pressure to obtain 9 g of 3-iodopropargyl phenylcarbonate as an oily product.

$^1$H-NMR (CDCl$_3$):δ(ppm) 4.92 (2H, s), 7.0–7.6 (5H, m)

To 10 ml of a toluene solution containing 2.20 g (7.3 mmoles) of 3-iodopropargyl phenylcarbonate obtained above and 1.00 g (6.5 mmoles) of 3,5-dimethoxyaniline was added 0.29 g (7.3 mmoles) of 60% sodium hydride. After stirring overnight at room temperature, the reaction solution was poured into ice water and extracted with ethyl acetate. The organic layer was dried over anhydrous magnesium sulfate, and the solvent was removed by vaporization under reduced pressure.

The residue was collected and treated by thin layer chromatography (thickness, 2 mm; n-hexane: ethyl acetate=4:1) to obtain 1.8 g of 3-iodopropargyl N-(3,5-dimethoxyphenyl)carbamate.

m.p., 167°–168° C.

$^1$H-NMR (CDCl$_3$+DMSO-d$_6$):δ(ppm) 3.78 (6H, s), 4.90 (2H, s), 6.20 (1H, t, J=3Hz), 6.75 (2H, d, J=3Hz), 8.55 (1H, brs)

Some of the present compounds which can be produced by the above methods will be shown in Table 1.

TABLE 1

Carbamate derivatives represented by the general formula:

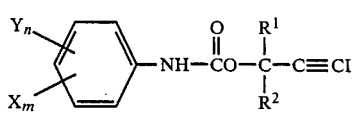

| Compound No. | X$_m$ | R$^1$ | R$^2$ | Physical constant |
|---|---|---|---|---|
| 1 | C$_2$H$_5$O– (2,4-di C$_2$H$_5$O phenyl) | H | H | m.p. 114–115° C. |
| 2 | CH$_3$O– (3-position phenyl) | H | H | m.p. 107–108° C. |
| 3 | C$_2$H$_5$O– (4-position phenyl) | H | H | m.p. 119–120° C. |
| 4 | CF$_3$– (3-position phenyl) | H | H | n$_D^{19}$ 1.5490 |
| 5 | CF$_3$– (4-position phenyl) | H | H | m.p. 104–105° C. |
| 6 | C$_2$H$_5$O– (3-position phenyl) | H | H | m.p. 82–83° C. |
| 7 | O$_2$N– (4-position phenyl) | H | H | m.p. 169–170° C. |

TABLE 1-continued
Carbamate derivatives represented by the general formula:
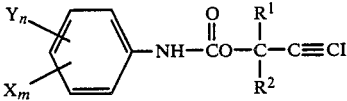
| Compound No. | $X_m$ $Y_n$ | $R^1$ | $R^2$ | Physical constant |
|---|---|---|---|---|
| 8 | 3-NO$_2$-C$_6$H$_4$- | H | H | m.p. 150–151° C. |
| 9 | 2-CF$_3$-C$_6$H$_4$- | H | H | m.p. 78–79° C. |
| 10 | 4-(n-C$_4$H$_9$O)-C$_6$H$_4$- | H | H | m.p. 124–125° C. |
| 11 | 2-OCH$_3$-C$_6$H$_4$- | H | H | $n_D^{20}$ 1.6010 |
| 12 | 2,4-(OCH$_3$)$_2$-C$_6$H$_3$- | H | H | m.p. 126–127° C. |
| 13 | 2,4-(OCH$_3$)$_2$-C$_6$H$_3$- | H | H | m.p. 99–100° C. |
| 14 | 3-NC-C$_6$H$_4$- | H | H | m.p. 145–146° C. |
| 15 | 4-NC-C$_6$H$_4$- | H | H | m.p. 170–171° C. |
| 16 | 3,5-(CH$_3$O)$_2$-C$_6$H$_3$- | H | H | m.p. 167–168° C. |

TABLE 1-continued

Carbamate derivatives represented by the general formula:

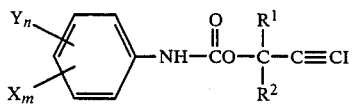

| Compound No. | $X_m$ / $Y_n$ (phenyl) | $R^1$ | $R^2$ | Physical constant |
|---|---|---|---|---|
| 17 | 3-Cl, 4-(CH≡CCH₂O), 5-(CH≡CCH₂O)-phenyl | H | H | $n_D^{22}$ 1.5889 |
| 18 | 3-Cl, 4-(C₂H₅O), 5-(CH₃OCH₂)-phenyl | H | H | m.p. 81–83° C. |
| 19 | 4-CH₃O-phenyl | H | H | m.p. 135–136° C. |
| 20 | 4-(n-C₃H₇O)-phenyl | H | H | m.p. 104–105.5° C. |
| 21 | 4-(iso-C₄H₉O)-phenyl | H | H | m.p. 102–103° C. |
| 22 | 4-(n-C₅H₁₁O)-phenyl | H | H | m.p. 117–118° C. |
| 23 | 4-(sec-C₅H₁₁O)-phenyl | H | H | m.p. 61.5–62.5° C. |
| 24 | 4-(N-C₈H₁₇O)-phenyl | H | H | m.p. 86–87° C. |
| 25 | 4-(n-C₁₂H₂₅O)-phenyl | H | H | m.p. 94.5–95.5° C. |
| 26 | 3-Cl, 4-(iso-C₃H₇O), 5-F-phenyl | H | H | m.p. 71–72° C. |

TABLE 1-continued
Carbamate derivatives represented by the general formula:
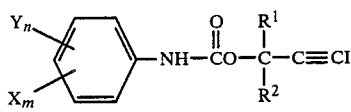
| Compound No. |  | R¹ | R² | Physical constant |
|---|---|---|---|---|
| 27 | 2-Cl, 4-CHF₂O-phenyl | H | H | m.p. 146–149° C. |
| 28 | 4-CHF₂CF₂O-phenyl | H | H | m.p. 127–128° C. |
| 29 | 4-CH₃S-phenyl | H | H | m.p. 145–146° C. |
| 30 | 3,4-(CH₃O)₂-phenyl | H | H | m.p. 162–164° C. |
| 31 | 4-C₂H₅O₂C-phenyl | H | H | m.p. 175–176° C. |
| 32 | 2,6-Cl₂-4-O₂N-phenyl | H | H | m.p. 222–224° C. |
| 33 | 2,4-(O₂N)₂-phenyl | H | H | m.p. 88–89° C. |
| 34 | 2-NO₂-4-CH₃O-phenyl | H | H | m.p. 125–126° C. |
| 35 | 3-OCH₃-4-O₂N-phenyl | H | H | m.p. 152–153° C. |

TABLE 1-continued

Carbamate derivatives represented by the general formula:

$$Y_n\text{-}X_m\text{-}C_6H_3\text{-}NH\text{-}CO\text{-}O\text{-}CR^1R^2\text{-}C\equiv CCl$$

| Compound No. | $X_m$ / $Y_n$ (aryl substitution) | $R^1$ | $R^2$ | Physical constant |
|---|---|---|---|---|
| 36 | 3,4-di(C$_2$H$_5$O)-C$_6$H$_3$- | H | CH$_3$ | m.p. 132–133° C. |
| 37 | 4-C$_2$H$_5$O-C$_6$H$_4$- | H | CH$_3$ | m.p. 134–135° C. |
| 38 | 3-C$_2$H$_5$O-C$_6$H$_4$- | H | CH$_3$ | m.p. 108–109° C. |
| 39 | 3-CH$_3$O-C$_6$H$_4$- | H | CH$_3$ | $n_D^{20}$ 1.5682 |
| 40 | 4-n-C$_4$H$_9$O-C$_6$H$_4$- | H | CH$_3$ | m.p. 96–97° C. |
| 41 | 3-NC-C$_6$H$_4$- | H | CH$_3$ | $n_D^{22.5}$ 1.5995 |
| 42 | 4-NC-C$_6$H$_4$- | H | CH$_3$ | $^1$H—NMR (CDCl$_3$): δ (ppm) 1.51 (3H, d, J=6Hz) 5.48 (1H, q, J=6Hz), 6.83 (1H, brs), 7.43 (4H, s) |
| 43 | 4-C$_2$H$_5$O-C$_6$H$_4$- | CH$_3$ | CH$_3$ | m.p. 132.5–133° C. |
| 44 | 3,4-di(C$_2$H$_5$O)-C$_6$H$_3$- | CH$_3$ | CH$_3$ | m.p. 122–123° C. |
| 45 | 4-CH$_3$O-C$_6$H$_4$- | H | CH$_3$ | m.p. 113–114° C. |

TABLE 1-continued
Carbamate derivatives represented by the general formula:
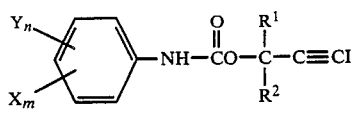
| Compound No. | $X_m$ / $Y_n$-phenyl | $R^1$ | $R^2$ | Physical constant |
|---|---|---|---|---|
| 46 | n-$C_3H_7$O—(4-) | H | $CH_3$ | m.p. 109–111° C. |
| 47 | iso-$C_4H_9$O—(4-) | H | $CH_3$ | m.p. 91–92° C. |
| 48 | n-$C_5H_{11}$O—(4-) | H | $CH_3$ | m.p. 83–84° C. |
| 49 | sec-$C_5H_{11}$O—(4-) | H | $CH_3$ | $n_D^{20}$ 1.5508 |
| 50 | n-$C_8H_{17}$O—(4-) | H | $CH_3$ | m.p. 78–79° C. |
| 51 | n-$C_{12}H_{25}$O—(4-) | H | $CH_3$ | m.p. 84–85° C. |
| 52 | 3-Cl, 4-iso-$C_3H_7$O, 5-F | H | $CH_3$ | $n_D^{25}$ 1.5576 |
| 53 | 3-Cl, 4-$CHF_2$O | H | $CH_3$ | m.p. 116–118° C. |
| 54 | 4-$CHF_2CF_2$O | H | $CH_3$ | m.p. 98–95° C. |
| 55 | 4-$CH_3$S | H | $CH_3$ | m.p. 151–152° C. |

TABLE 1-continued

Carbamate derivatives represented by the general formula:

$$Y_n, X_m\text{-C}_6H_3\text{-NH-CO-O-C}(R^1)(R^2)\text{-C}\equiv CCl$$

| Compound No. | $X_m$, $Y_n$ substituted phenyl | $R^1$ | $R^2$ | Physical constant |
|---|---|---|---|---|
| 56 | 3,4-(CH$_3$O)$_2$-C$_6$H$_3$- | H | CH$_3$ | m.p. 131–132° C. |
| 57 | 4-(C$_2$H$_5$O$_2$C)-C$_6$H$_4$- | H | CH$_3$ | m.p. 193–194° C. |
| 58 | 4-CH$_3$O-3-NO$_2$-C$_6$H$_3$- | H | CH$_3$ | m.p. 152–153° C. |
| 59 | 3-O$_2$N-4-OCH$_3$-C$_6$H$_3$- | H | CH$_3$ | m.p. 104–105° C. |
| 60 | 4-O$_2$N-C$_6$H$_4$- | H | CH$_3$ | $n_D^{23}$ 1.6061 |
| 61 | 3-O$_2$N-C$_6$H$_4$- | H | CH$_3$ | m.p. 111–112° C. |
| 62 | 4-(CH$_2$=CHCH$_2$O)-C$_6$H$_4$- | H | H | m.p. 97–98° C. |

Formulation examples will be shown. In the examples, all parts are by weight.

FORMULATION EXAMPLE 1

Fifty parts of each of the present compounds (1) to (62), 3 parts of calcium lignosulfonate, 2 parts of sodium lauryl sulfate and 45 parts of synthetic hydrated silicon dioxide are well pulverized and mixed to obtain a wettable powder of each compound.

FORMULATION EXAMPLE 2

Twenty-five parts of each of the present compounds (1) to (62), 3 parts of polyoxyethylene sorbitan monooleate, 3 parts of CMC and 69 parts of water are mixed and wet-pulverized until the particle size of the active ingredient is reduced to 5 microns or less to obtain a suspension formulation of each compound.

FORMULATION EXAMPLE 3

Two parts of each of the present compounds (1) to (62), 88 parts of kaolin clay and 10 parts of talc are well pulverized and mixed to obtain a dust of each compound.

FORMULATION EXAMPLE 4

Twenty parts of each of the present compounds (1) to (62), 14 parts of polyoxyethylene styrylphenyl ether, 6 parts of calcium dodecylbenzenesulfonate and 60 parts of xylene are well mixed to obtain an emulsifiable concentrate of each compound.

FORMULATION EXAMPLE 5

Two parts of each of the present compounds (1) to (62), 1 part of synthetic hydrated silicon dioxide, 2 parts of calcium lignosulfonate, 30 parts of bentonite and 65 parts of kaolin clay are well pulverized and mixed, well kneaded with water, granulated and dried to obtain a granule of each compound.

Next, the usefulness of the present compounds as an agricultural and horticultural fungicide will be shown with reference to the following test examples. In the test examples, the present compounds are shown by Compound No. in Table 1, and compounds used as a control are shown by Compound symbol in Table 2.

TABLE 2

| Compound symbol | Structural formula | Remarks |
|---|---|---|
| A | $CuSO_4 \cdot XCu(OH)_2 \cdot YCa(OH)_2 \cdot ZH_2O$ | Commercial product (copper wettable powder) |
| B | 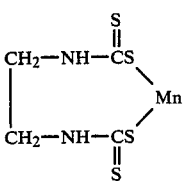 | Commercial product (Maneb) |

The controlling activity was expressed in six stages described below, 5, 4, 3, 2, 1, 0, according to the condition of disease of test plants at the time of examination, i.e. the degrees of colony and infected area on the leaves, stems, etc., observed with the naked eyes.

5: Neither colony nor infected area is observed.
4: About 10% of colony or infected area is observed.
3: About 30% of colony or infected area is observed.
2: About 50% of colony or infected area is observed.
1: About 70% of colony or infected area is observed
0: More than about 70% of colony or infected area is observed, there being no difference in the condition of disease between the treated and untreated plots.

TEST EXAMPLE 1

Controlling test on late blight of potato (*Phytophthora infestans*) (preventive effect)

Sandy loam was filled in plastic pots, and potato (var., Danshaku) was sowed and cultivated into seedlings for 20 days in a greenhouse. The wettable powder of each test compound prepared according to Formulation Example 1 was diluted with water to a prescribed concentration and foliar-sprayed onto the seedlings so that the spray liquor was thoroughly attached to the leaf surface. After spraying, the seedlings were inoculated by spraying the spore suspension of *Phytophthora infestans*. After inoculation, the seedlings were cultivated firstly at 20° C. for 1 day under a highly humid conditions, and then under lighting for 5 days to examine the controlling activity. The results are shown in Table 3.

TABLE 3

| Test compound | | Controlling activity |
|---|---|---|
| Compound No. | Application concentration of active ingredient (ppm) | |
| 1 | 200 | 5 |
| 2 | 200 | 5 |
| 3 | 200 | 5 |
| 5 | 200 | 5 |
| 6 | 200 | 5 |
| 7 | 200 | 5 |
| 8 | 200 | 5 |
| 9 | 200 | 5 |
| 10 | 200 | 5 |
| 11 | 200 | 5 |
| 12 | 200 | 5 |
| 13 | 200 | 5 |
| 14 | 200 | 5 |
| 16 | 200 | 5 |
| 17 | 200 | 5 |
| 18 | 200 | 5 |
| 19 | 200 | 5 |
| 20 | 200 | 5 |
| 23 | 200 | 5 |
| 30 | 200 | 5 |
| 37 | 200 | 5 |
| 38 | 200 | 5 |
| 39 | 200 | 5 |
| 40 | 200 | 5 |
| 46 | 200 | 5 |
| 48 | 200 | 5 |
| 49 | 200 | 5 |
| A | 200 | 3 |
| B | 200 | 4 |

TEST EXAMPLE 2

Controlling test on downy mildew of grape (*Plasmopara viticola*) (preventive effect)

Sandy loam was filled in plastic pots, and grape was sowed and cultivated into seedlings in the 5th to 6th true leaf stage for 50 days in a greenhouse. The wettable powder of each test compound prepared according to Formulation Example 1 was diluted with water to a prescribed concentration and foliar-sprayed onto the seedlings so that the spray liquor was thoroughly attached to the leaf surface.

After spraying, the seedlings were inoculated by spraying the spore suspension of *Plasmopara viticola*. After inoculation, the seedlings were cultivated firstly at 20° C. for 1 day under a highly humid condition and then under lighting for 8 days to examine the controlling activity. The results are shown in Table 4.

TABLE 4

| Test compound | | Controlling activity |
|---|---|---|
| Compound No. | Application concentration of active ingredient (ppm) | |
| 5 | 200 | 5 |
| 6 | 200 | 5 |
| 7 | 200 | 5 |
| 9 | 200 | 5 |
| 10 | 200 | 5 |
| 11 | 200 | 5 |
| 12 | 200 | 5 |
| 13 | 200 | 5 |
| 19 | 200 | 5 |
| 25 | 200 | 5 |
| 27 | 200 | 5 |
| 28 | 200 | 5 |
| 34 | 200 | 5 |
| 38 | 200 | 5 |
| 40 | 200 | 5 |
| 48 | 200 | 5 |
| 49 | 200 | 5 |
| A | 200 | 2 |

TEST EXAMPLE 3

Controlling test on eye spot of wheat
(*Pseudocercosporella herpotrichoides*) (preventive effect)

Sandy loam was filled in plastic pots, and wheat (var., Norin No. 73) was sowed and cultivated into seedlings for 10 days in a greenhouse. The wettable powder of each test compound prepared according to Formulation Example 1 was diluted with water to a prescribed concentration and foliar-sprayed onto the seedlings so that the spray liquor was thoroughly attached to the leaf surface. After spraying, the seedlings were air-dried and inoculated by spraying the spore suspension of *Pseudocercosporella herpotrichoides*. After inoculation, the seedlings were cultivated firstly at 15° C. in the dark under a highly humid condition for 4 days and then under lighting and a highly humid condition for 4 days to examine the controlling activity. The results are shown in Table 5.

TABLE 5

| Test compound | | |
|---|---|---|
| Compound No. | Application concentration of active ingredient (ppm) | Controlling activity |
| 3 | 500 | 4 |
| 7 | 500 | 5 |
| 9 | 500 | 4 |
| A | 500 | 1 |

TEST EXAMPLE 4

Controlling test on scab of apple (*Venturia inaequalis*)
(Preventive effect)

Sandy loam was filled in plastic pots, and apple was sowed and cultivated into seedlings in the 4th to 5th true leaf stage for 20 days in a greenhouse. The wettable powder of each test compound prepared according to Formulation Example 1 was diluted with water to a prescribed concentration and foliar-sprayed onto the seedlings so that the spray liquor was thoroughly attached to the leaf surface.

After spraying, the seedlings were inoculated by spraying the spore suspension of *Venturia inaequalis*. After inoculation, the seedlings were cultivated firstly at 15° C. under a highly humid condition for 4 days and then under lighting for 15 days to examine the controlling activity. The results are shown in Table 6.

TABLE 6

| Test compound | | |
|---|---|---|
| Compound No. | Application concentration of active ingredient (ppm) | Controlling activity |
| 5 | 200 | 4 |
| 9 | 200 | 4 |
| 11 | 200 | 4 |
| 18 | 200 | 5 |
| 19 | 200 | 4 |
| 20 | 200 | 5 |
| 21 | 200 | 4 |
| 33 | 200 | 5 |
| 34 | 200 | 4 |
| 35 | 200 | 4 |
| 58 | 200 | 4 |
| 59 | 200 | 4 |
| 60 | 200 | 5 |
| A | 200 | 3 |

TEST EXAMPLE 5

Controlling test on speckled leaf blotch of wheat
(*Septoria tritici*) (preventive effect)

Sandy loam was filled in plastic pots, and wheat (var., Norin No. 73) was sowed and cultivated into seedlings for 8 days in a greenhouse. The wettable powder of each test compound prepared according to Formulation example 1 was diluted with water to a prescribed concentration and foliar-sprayed onto the seedlings so that the spray liquor was thoroughly attached to the leaf surface. After spraying, the seedlings were inoculated by spraying the spore suspension of *Septoria tritici*. After inoculation, the seedlings were cultivated firstly at 15° C. in the dark under a highly humid condition for 3 days and then at 15° C. under lighting for 15 days to examine the controlling activity. The results are shown in Table 7.

TABLE 7

| Test compound | | |
|---|---|---|
| Compound No. | Application concentration of active ingredient (ppm) | Controlling activity |
| 4 | 500 | 5 |
| 8 | 500 | 5 |
| 14 | 500 | 5 |
| 15 | 500 | 5 |
| 19 | 500 | 5 |
| 20 | 500 | 5 |
| 21 | 500 | 5 |
| 22 | 500 | 5 |
| 41 | 500 | 5 |
| 42 | 500 | 5 |
| 46 | 500 | 5 |
| 47 | 500 | 5 |
| 48 | 500 | 5 |
| 49 | 500 | 5 |
| B | 500 | 3 |

TEST EXAMPLE 6

Controlling test on gray mold of cucumber (*Botrytis cinerea*) (preventive effect)

Sandy loam was filled in plastic pots, and cucumber (var., Sagamihanjiro) was sowed and cultivated into seedlings in the cotyledonous stage for 14 days in a greenhouse. The wettable powder of each test compound prepared according to Formulation example 1 was diluted with water to a prescribed concentration and foliar-sprayed onto the seedlings so that the spray liquor was thoroughly attached to the leaf surface. After spraying, the seedlings were inoculated with the mycelium suspension of *Botrytis cinerea*. After inoculation, the seedlings were cultivated at 15° C. under a highly humid condition for 4 days to examine the controlling activity. The results are shown in Table 8.

TABLE 8

| Test compound | | |
|---|---|---|
| Compound No. | Application concentration of active ingredient (ppm) | Controlling activity |
| 1 | 500 | 4 |
| 17 | 500 | 4 |
| 18 | 500 | 5 |
| 36 | 500 | 4 |
| 44 | 500 | 4 |
| A | 500 | 2 |
| B | 500 | 0 |

TEST EXAMPLE 7

Controlling test on early blight of tomato (*Alternaria solani*) (preventive effect)

Sandy loam was filled in plastic pots, and tomato (var., Ponteroza) was sowed and cultivated into seedlings in the third to fourth true leaf stage for 30 days in a greenhouse. The suspension formulation of each test compound prepared according to Formulation example 2 was diluted with water to a prescribed concentration and foliar-sprayed onto the seedlings so that the spray liquor was thoroughly attached to the leaf surface. After spraying, the seedlings were inoculated by spraying the spore suspension of *Alternaria solani*. After inoculation, the seedlings were cultivated at 23° C. under a highly humid condition for 6 days to examine the controlling activity. The results are shown in Table 9.

TABLE 9

| Test compound | | |
|---|---|---|
| Compound No. | Application concentration of active ingredient (ppm) | Controlling activity |
| 1 | 400 | 4 |
| 2 | 400 | 5 |
| 7 | 400 | 4 |
| 8 | 400 | 5 |
| 36 | 400 | 5 |
| 37 | 400 | 5 |
| 38 | 400 | 5 |
| 39 | 400 | 4 |
| 45 | 400 | 4 |

What is claimed is:

1. A compound represented by the general formula,

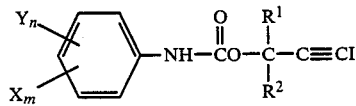

wherein X, which may be the same or different, represents a cyano, nitro, halogenated lower alkyl, $C_1$-$C_{12}$ alkoxy, lower alkoxy-substituted lower alkyl, lower alkenyloxy, lower alkynyloxy, halogenated lower alkoxy, lower alkoxycarbonyl or lower alkylthio group, $R^1$ and $R^2$, which may be the same or different, represent a hydrogen atom or a methyl group, Y represents a chlorine atom, m represents an integer of from 1 to 5, and n represents an integer of from 0 to 4, the sum of m and n being less than 6.

2. A compound according to claim 1, wherein X, which may be the same or different, represents a cyano, nitro, halogenated $C_1$-$C_3$ alkyl, $C_1$-$C_{12}$ alkoxy, $C_1$-$C_4$ alkoxy-substituted $C_1$-$C_3$ alkyl, $C_2$-$C_4$ alkenyloxy, $C_3$-$C_5$ alkynyloxy, halogenated $C_1$-$C_4$ alkoxy, $C_1$-$C_3$ alkoxycarbonyl or $C_1$-$C_4$ alkylthio group, $R^1$ and $R^2$ each represents a hydrogen atom, n is equal to zero and m represents an integer of from 1 to 5.

3. A compound according to claim 1, wherein X, which may be the same or different, represents a cyano, nitro, halogenated $C_1$-$C_2$ alkyl or $C_1$-$C_5$ alkoxy, $R^1$ and $R^2$ each represents a hydrogen atom, n is equal to zero and m represents an integer of from 1 to 3.

4. A fungicidal composition which comprises as an active ingredient a fungicidally effective amount of a compound represented by the general formula,

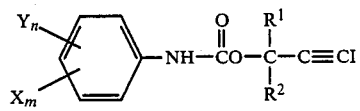

wherein X, which may be the same or different, represents a cyano, nitro, halogenated lower alkyl, $C_1$-$C_{12}$ alkoxy, lower alkoxy-substituted lower alkyl, lower alkenyloxy, lower alkynyloxy, halogenated lower alkoxy, lower alkoxy-carbonyl or lower alkylthio group, $R^1$ and $R^2$, which may be the same or different, represent a hydrogen atom or a methyl group, Y represents a chlorine atom, m represents an integer of from 1 to 5, and n represents an integer of from 0 to 4, the sum of m and n being less than 6, and an inert carrier.

5. A method for controlling plant pathogenic fungi which comprises applying a fungicidally effective amount of a compound represented by the general formula,

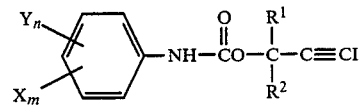

wherein X, which may be the same or different, represents a cyano, nitro, halogenated lower alkyl, $C_1$-$C_{12}$ alkoxy, lower alkoxy-substituted lower alkyl, lower alkenyloxy, lower alkynyloxy, halogenated lower alkoxy, lower alkoxy-carbonyl or lower alkylthio group, $R^1$ and $R^2$, which may be the same or different represent a hydrogen atom or a methyl group, Y represents a chlorine atom, m represents an integer of from 1 to 5, and n represents an integer of from 0 to 4, the sum of m and n being less than 6, to plant pathogenic fungi.

6. A compound according to claim 1 wherein n is equal to zero.

* * * * *

UNITED STATES PATENT AND TRADEMARK OFFICE
CERTIFICATE OF CORRECTION

PATENT NO.   : 4,841,088
DATED        : JUNE 20, 1989
INVENTOR(S)  : Tomoyuki KUSABA et al It is certified that error appears in the above-identified patent and that said Letters Patent is hereby corrected as shown below:

Column 7, line 48, change "m.p., 134°-135°C." to -- 132.5-133°C --;

Column 7, line 62, change "m.p., 150°-151° C." to -- 169°-170°C --.

Column 10, Table 1, Compound No. 2, change "m.p. 107-108°" to -- 106.5°-107° C. --.

Signed and Sealed this

Fourteenth Day of May, 1991

Attest:

HARRY F. MANBECK, JR.

*Attesting Officer*   Commissioner of Patents and Trademarks